US012779225B2

(12) United States Patent
Sinclair et al.

(10) Patent No.: US 12,779,225 B2
(45) Date of Patent: Nov. 3, 2026

(54) SYSTEMS AND METHODS FOR MONITORING NEURAL ACTIVITY

(71) Applicant: Boston Scientific Neuromodulation Corporation, Valencia, CA (US)

(72) Inventors: Nicholas Sinclair, East Melbourne (AU); Hugh McDermott, East Melbourne (AU); Arthur Wesley Thevathasan, East Melbourne (AU); James Fallon, East Melbourne (AU)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 993 days.

(21) Appl. No.: 17/794,754

(22) PCT Filed: Jan. 21, 2021

(86) PCT No.: PCT/AU2021/050035
§ 371 (c)(1),
(2) Date: Jul. 22, 2022

(87) PCT Pub. No.: WO2021/146774
PCT Pub. Date: Jul. 29, 2021

(65) Prior Publication Data

US 2023/0111085 A1 Apr. 13, 2023

(30) Foreign Application Priority Data

Jan. 24, 2020 (AU) ................................ 2020900195

(51) Int. Cl.
*A61N 1/36* (2006.01)
*A61N 1/05* (2006.01)

(52) U.S. Cl.
CPC ....... *A61N 1/36135* (2013.01); *A61N 1/3606* (2013.01); *A61N 1/36171* (2013.01); *A61N 1/36178* (2013.01); *A61N 1/0534* (2013.01)

(58) Field of Classification Search
CPC .............. A61N 1/36135; A61N 1/3606; A61N 1/36171; A61N 1/36178; A61N 1/0534;
(Continued)

(56) References Cited

U.S. PATENT DOCUMENTS 8,099,170 B2 1/2012 Jensen et al.
2004/0019370 A1 1/2004 Gliner et al.
(Continued)

FOREIGN PATENT DOCUMENTS

CN 105848575 A 8/2016
CN 109689156 A 4/2019
(Continued)

OTHER PUBLICATIONS

Montgomery et al., "Mechanisms of action of deep brain stimulation (DBS)", Elsevier, Neuroscience & Biobehavioral Reviews 32, pp. 388-407, 2008.
(Continued)

*Primary Examiner* — Carl H Layno
*Assistant Examiner* — Maria Catherine Anthony
(74) *Attorney, Agent, or Firm* — Lewis & Reese, PLLC

(57) ABSTRACT

A method of neurostimulation includes applying a probe signal to an electrode implanted in or near a target neural structure of the brain. The method further includes detecting a first response from the target neural structure evoked by the probe signal and determining a first time period between application of the probe signal and a first temporal feature of the response. Further, the method includes generating a therapeutic signal comprising a plurality of pulses, at least two of the plurality of pulses separated by the first time period, and applying the therapeutic signal to the electrode or another electrode implanted in or near the target neural structure.

33 Claims, 11 Drawing Sheets

(58) Field of Classification Search
CPC ............ A61N 1/36064; A61N 1/36067; A61N 1/3615; A61N 1/36175; A61N 1/36139; A61N 1/36146; A61N 1/36132; A61B 5/6868; A61B 5/377; A61B 5/4836; A61B 5/293; A61B 5/388
See application file for complete search history.

(56) References Cited

U.S. PATENT DOCUMENTS

| | | | |
|---|---|---|---|
| 2007/0179557 | A1 | 8/2007 | Maschino et al. |
| 2011/0137371 | A1 | 6/2011 | Giftakis et al. |
| 2011/0257708 | A1 | 10/2011 | Kramer et al. |
| 2015/0165206 | A1 | 6/2015 | Venkatesan et al. |
| 2019/0298992 | A1 | 10/2019 | Zhang et al. |
| 2019/0381318 | A1 | 12/2019 | Sinclair et al. |
| 2019/0388092 | A1 | 12/2019 | Thompson et al. |
| 2019/0388692 | A1 | 12/2019 | Dinsmoor et al. |

FOREIGN PATENT DOCUMENTS

| | | | | |
|---|---|---|---|---|
| EP | 2945698 | B1 | 12/2019 | |
| JP | 2019-529007 | A | 10/2019 | |
| WO | WO-2018027259 | A1 * | 2/2018 | ........... A61B 5/6868 |
| WO | WO-2018033732 | A1 | 2/2018 | |
| WO | WO-2018213872 | A1 | 11/2018 | |
| WO | WO-2019210371 | A1 | 11/2019 | |

OTHER PUBLICATIONS

Cagnan et al., "Stimulating at the right time: phase-specific deep brain stimulation", Brain, A Journal of Neurology, pp. 1-14, Dec. 22, 2016.
International Search Report issued in PCT Appl. No. PCT/AU2021/050035 dated Feb. 26, 2021.
Written Opinion issued in PCT Appl. No. PCT/AU2021/050035 dated Feb. 26, 2021.

* cited by examiner

SYSTEMS AND METHODS FOR MONITORING NEURAL ACTIVITY

CROSS-REFERENCE TO RELATED APPLICATION

This application claims priority to Australian provisional patent application no. 2020900195, filed 24 Jan. 2020, the entire contents of which is incorporated herein by reference.

TECHNICAL FIELD

The present disclosure relates to deep brain stimulation (DBS) and, in particular, methods and systems of monitoring neural activity during DBS.

BACKGROUND

Deep brain stimulation (DBS) is an established therapy for movement disorders as well as other neurological disorders, including epilepsy, obsessive compulsive disorder, and depression. DBS is typically administered to patients whose symptoms cannot be adequately controlled by medication alone. DBS involves surgically implanting electrodes in or near to specific neural structures of the brain, typically in the subthalamic nucleus (STN), the globus pallidus interna (GPi), and/or the thalamus. Electrodes are connected to a neurostimulator usually implanted within the body and configured to deliver electrical pulses into target areas. It is believed that this electrical stimulation disrupts abnormal brain activity causally linked to a patient's symptoms. Stimulation parameters can be adjusted using a controller external to the body, remotely connected to the neurostimulator.

Whilst established DBS technology has proven to be effective in alleviating movement disorder symptoms, there are several limitations to state of the art devices. In particular, established techniques for intraoperative testing of DBS electrodes to ensure correct positioning in the brain, such as x-ray imaging, microelectrode recordings, and clinical assessment can be inaccurate. Consequently, electrodes are often implanted in suboptimal locations, resulting in diminished therapeutic outcomes and unwanted side-effects. After implantation, DBS devices require manual adjustment by a clinician. This typically involves the clinician adjusting parameters of the stimulus based on a largely subjective assessment of immediate or short-term improvement of the patient's symptoms. Since therapeutic effects can be slow to emerge and because the DBS parameter space is large, the task of finding a preferred set of parameters is time- and cost-inefficient, and can lead to suboptimal therapeutic outcomes. In addition, the constant, non-varying application of electrical stimulation using conventional DBS can also lead to suboptimal therapeutic outcomes, including unwanted side effects, as well as reduced battery life of DBS stimulators.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

In one aspect, there is provided a method of neurostimulation, comprising: a. applying a probe signal to an electrode implanted in or near a target neural structure of the brain; b. detecting a first response from the target neural structure evoked by the probe signal; c. determining a first time period between application of the probe signal and a first temporal feature of the first response; d. generating a therapeutic signal comprising a plurality of pulses, at least two of the plurality of pulses separated by the first time period; e. applying the therapeutic signal to the electrode or another electrode implanted in or near the target neural structure.

The method may further comprise: repeating steps a to d.

The method may further comprise continuously applying the therapeutic signal to the electrode between repetitions of steps a to d.

In some embodiments, at least three of the plurality of pulses are separated by the first time period.

The method may further comprise: f. determining a second time period between application of the probe signal and a second temporal feature of the first oscillatory response.

At least two of the plurality of pulses may be separated by the second time period.

In some embodiments, a first one of the at least two of the plurality of pulses separated by the first time period and a first one of the at least two of the plurality of pulses separated by the second time period are the same pulse.

The probe signal may have a fixed amplitude. The probe signal may have a fixed average frequency whilst being aperiodic in nature.

Completion of application of the probe signal and commencement of application of the therapeutic signal may be separated by a measurement time period in which no signal is applied to the electrode or the other electrode implanted in or near the target neural structure.

The method may further comprise: detecting a second response from the target neural structure evoked by the therapeutic signal; and determining a difference between a common temporal feature in the first and second responses. The difference may comprise a difference in amplitude of the first and second responses. Determining the difference may comprise determining that the common temporal feature is suppressed in the second response relative to the first response.

The method may further comprise: adjusting the amplitude of the therapeutic signal in dependence on the difference.

The method may further comprise, after detecting the first oscillatory response and before determining the first time period: determining that the amplitude of the first oscillatory response is below a threshold amplitude; and increasing the amplitude of and re-applying the probe signal until the amplitude of the first oscillatory response is at or greater than the threshold amplitude.

In some embodiments, a frequency of pulses of the plurality of pulses other than the at least two pulses separated by the first time period is set such that an average frequency of pulses in the plurality of pulses is within a threshold range of a predetermined therapeutic frequency. For example, the at least two pulses may be repeated at a predetermined therapeutic frequency. The at least two pulses may be a pulse pair or a pulse triple. In any case, the first time period between the at least two pulses may be different to the time period between repetitions (i.e. time between the last pulse of a previous repetition and the first pulse of the subsequent repetition). In another example the plurality of pulses are provided as part of an ongoing pulse train presented at the predetermined therapeutic frequency on average, although the temporal separation of at least some of the pulses is individually adjusted as described above.

In some embodiments, the predetermined therapeutic frequency may be between approximately 70 Hz and approximately 200 Hz, for example around 130 Hz.

The temporal feature may be one or more of: a peak in the response; a trough in the response; a crossing of the response through a predetermined amplitude; a gradient of the response.

In another aspect, there is provided a method of neurostimulation, comprising: applying a stimulus to an electrode implanted in or near a target neural structure of the brain, the stimulus comprising a plurality of pulses; detecting a response from the target neural structure evoked by the stimulus; determining a first time period between application of the stimulus and a first temporal feature of the first response; adjusting the stimulus such that at least two of the plurality of pulses are separated by the first time period; applying the adjusted stimulus to the electrode.

In another aspect, there is provided a neurostimulation system, comprising: a lead having at least one electrode adapted for implantation in or near a target neural structure in the brain; a signal generator selectively coupled to one or more of the at least one electrode and configured to: a. apply a probe signal to one of the at least one electrode implanted in or near a target neural structure of the brain; and one or more processors configured to: b. detect at the at least one electrode a first response from the target neural structure evoked by the probe signal; c. determine a first time period between application of the probe signal and a first temporal feature of the first response; and d. generate a therapeutic signal comprising a plurality of pulses, at least two of the plurality of pulses separated by the first time period. The signal generator may be further configured to: e. apply the therapeutic signal to the at least one electrode or another electrode implanted in or near the target neural structure.

The signal generator and the one or more processors may be further configured to: repeat steps a to d. The signal generator may be configured to continuously apply the therapeutic signal to the electrode between repetitions of steps a to d.

In some embodiments, at least three of the plurality of pulses are separated by the first time period.

The one or more processors may be further configured to: f. determine a second time period between application of the probe signal and second temporal feature of the first oscillatory response. At least two of the plurality of pulses may be separated by the second time period.

In some embodiments, a first one of the at least two of the plurality of pulses separated by the first time period and a first one of the at least two of the plurality of pulses separated by the second time period are the same pulse.

The probe signal has a fixed amplitude. The probe signal may have a fixed average frequency.

In some embodiments, completion of application of the probe signal and commencement of application of the therapeutic signal may be separated by a measurement time period in which no signal is applied to the electrode or the other electrode implanted in or near the target neural structure.

The one or more processors may be further configured to: detect a second response from the target neural structure evoked by the therapeutic signal; and determine a difference between a common temporal feature in the first and second responses. The difference may comprise a difference in amplitude of the first and second responses. Determining the difference may comprise determining that the common temporal feature is suppressed in the second response relative to the first response.

The one or more processors may be further configured to: adjust the amplitude of the therapeutic signal in dependence on the difference.

The one or more processors may be further configured to, after detecting the first oscillatory response and before determining the first time period: determine that the amplitude of the first oscillatory response is below a threshold amplitude; and increase the amplitude of the probe signal being applied by the signal generator until the amplitude of the first oscillatory response is at or greater than the threshold amplitude.

In some embodiments, a frequency of pulses of the plurality of pulses other than the at least two pulses separated by the first time period may be set such that an average frequency of pulses in the plurality of pulses is within a threshold range of a predetermined therapeutic frequency. The predetermined therapeutic frequency may be between approximately 70 Hz and approximately 200 Hz.

The temporal feature may be one or more of: a peak in the response; a trough in the response; a crossing of the response through a predetermined amplitude; a gradient of the response.

In another aspect, there is provided a system of neurostimulation, comprising: a lead having at least one electrode adapted for implantation in or near a target neural structure in the brain; a signal generator selectively coupled to one or more of the at least one electrode and configured to: apply a stimulus to an electrode implanted in or near a target neural structure of the brain, the stimulus comprising a plurality of pulses; one or more processors configured to: detect a response from the target neural structure evoked by the stimulus; determine a first time period between application of the stimulus and a first temporal feature of the first response; adjust the stimulus such that at least two of the plurality of pulses are separated by the first time period; the signal generator further configured to apply the adjusted stimulus to the electrode.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting examples with reference to the drawings, in which.

DESCRIPTION OF EMBODIMENTS

Embodiments of the present disclosure relate to improvements in neuro-stimulation in the brain. DBS devices typically apply a constant amplitude stimulus to a target area of the brain at a constant frequency. For example therapeutic stimulation is typically applied at a frequency between 70 Hz and 200 Hz, for example 130 Hz. The inventors have previously determined that application of such a stimulus evokes a neural response from the target area of the brain, and that the neural response comprises a resonant component (evoked resonant neural activity (ERNA)) comprising a multi-peaked neural response. Continuous DBS at conventional frequencies does not allow a long enough time window to observe the resonant activity. However, by monitoring the neural response after stimulation has ceased (by patterning the stimulation signal or otherwise), the resonant activity can be monitored and the efficacy of DBS stimulation can be ascertained and parameters of stimulation adjusted accordingly. Such techniques are described in detail in PCT (International) Patent Application Publication WO/2018/027259 ("the '259 Publication), the content of which is incorporated by reference in its entirety.

The inventors have since developed novel techniques for parameters of DBS therapy to maximise beneficial interaction between DBS and neural structures in the brain. The inventors have realised that by timing pulses of stimulation to coincide with temporal features of a neural response evoked by a previous applied stimulus, an interaction occurs between the timed stimulus and the neural response. Further, such interaction may cause a suppression of the neural response or an accentuation of the neural response which in turn can lead to an improvement in therapy or a condition of a patient.

Figure 1:
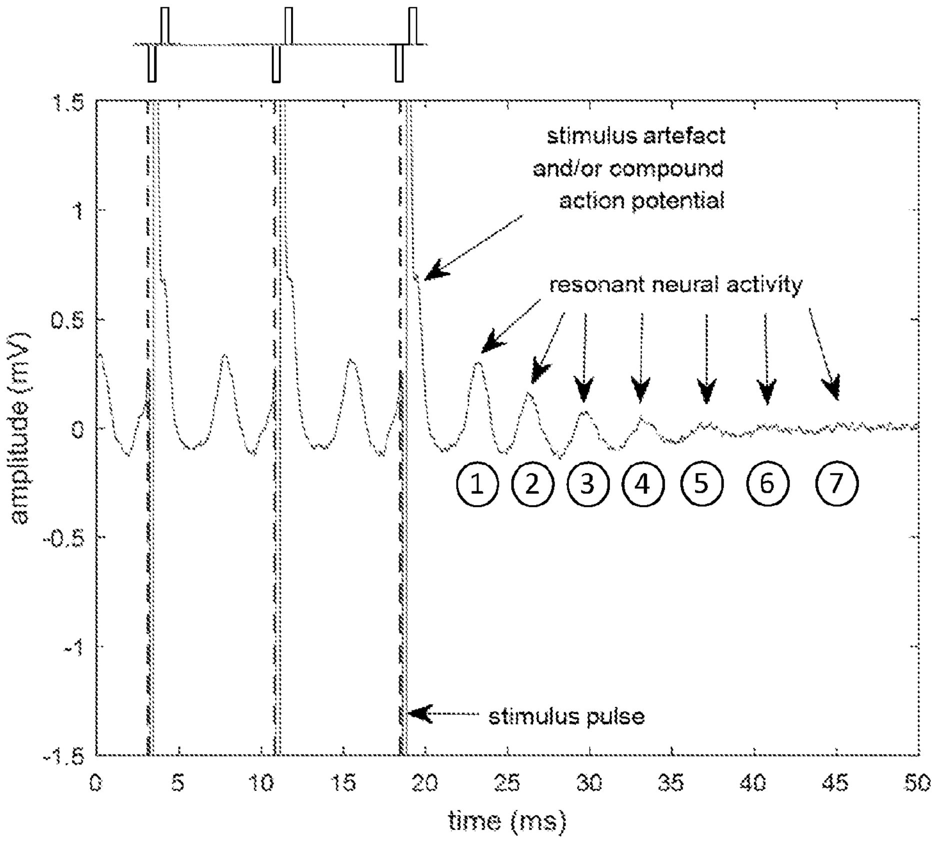
FIG. 1 is a graph illustrating resonance from a neural structure responsive to a deep brain stimulation (DBS) signal.

FIG. 1 graphically illustrates a response from a neural circuit stimulated by a 130 Hz signal delivered from a neurostimulator via an electrode lead, such as the 3387 electrode lead manufactured by Medtronic™, implanted in the subthalamic nucleus (STN) of a Parkinson's disease (PD) patient. Each response to a stimulus pulse comprises an evoked compound action potential (ECAP) component together with a component of evoked resonant neural activity (ERNA) occurring after the ECAP. The ECAP typically occurs within 1-2 milliseconds of the stimulus pulse. The graph shows the response to the last three consecutive pulses of a 60 second period of continuous stimulation followed by a period of no stimulation. It can be seen that the evoked resonant response to each of the first two stimulus pulses shown in FIG. 1 is cut short by the onset of the next stimulus pulse, such that only a single secondary peak is detected. However, the evoked resonant response to the third (and final) pulse is able to resonate for longer and so can be clearly seen in the form of a decaying oscillation with at least seven peaks for a post-stimulus period of about 30 milliseconds.

It is noted that the frequency of observed ERNA is typically in the range of 200 to 500 Hz, for example 250 to 450 Hz, or 300 to 400 Hz. It is noted that considerable variability exists in the frequency range of the observed ERNA across a patient population. A characteristic of ERNA which is not observed in spontaneous or background neural activity is that a temporal relationship exists between observed ERNA and the stimulus which induces the ERNA. For example, the observed ERNA is typically time-locked to the stimulus. In contrast, spontaneous or background neural activity has no consistent temporal relationship with deep brain stimulation pulses. Another characteristic which distinguishes ERNA from spontaneous or background neural activity is its amplitude, which is typically significantly higher than that of spontaneous or background neural activity. For example, beta-band spontaneous activity often has an average amplitude of less than 10 microvolts, whereas ERNA typically has an amplitude of hundreds of microvolts, for example greater than 100 microvolts, for example greater than 200 microvolts. Embodiments of the present disclosure may therefore monitor for evoked neural activity having amplitudes in the hundreds of microvolts range, for example at amplitudes greater than 100 microvolts or greater than 200 microvolts.

It is known for clinicians to control and adjust DBS parameters to elicit therapeutic effects in a patient. It is also known from the '529 Publication that by controlling the DBS parameters in certain ways, a non-therapeutic stimulus can be administered which evokes a resonant neural response (ERNA) in a patient without having any therapeutic impact or causing undesirable side effects. Such non-therapeutic stimuli can be used to reliably measure ERNA without causing sustained changes to the resonant neural circuit or the patient's symptomatic state. Non-therapeutic stimulation is preferably achieved by administering a stimulus comprising a short burst of pulses followed by a period of no stimulation, and the ERNA is measured during this period of no stimulation. By doing so, the total charge or energy provided to the patient is below a therapeutic threshold, and the measured ERNA provides information concerning the patient's natural state (without therapy). In an alternative embodiment, the overall charge or energy provided to the patient may be reduced by reducing the amplitude of the stimulation signal below a therapeutic threshold. However, doing so may also reduce the amplitude of peaks in the ERNA making it more difficult to observe. The '259 Publication also describes that patterned stimulation can be used to monitor and analyse evoked resonant neural activity during therapeutic stimulation of a patient. By patterning the stimulation signal, therapeutic stimulation can be maintained whilst providing time windows in which to monitor resonant responses past that of the first resonant peak or more preferably past two or more resonant peaks.

Figure 2:
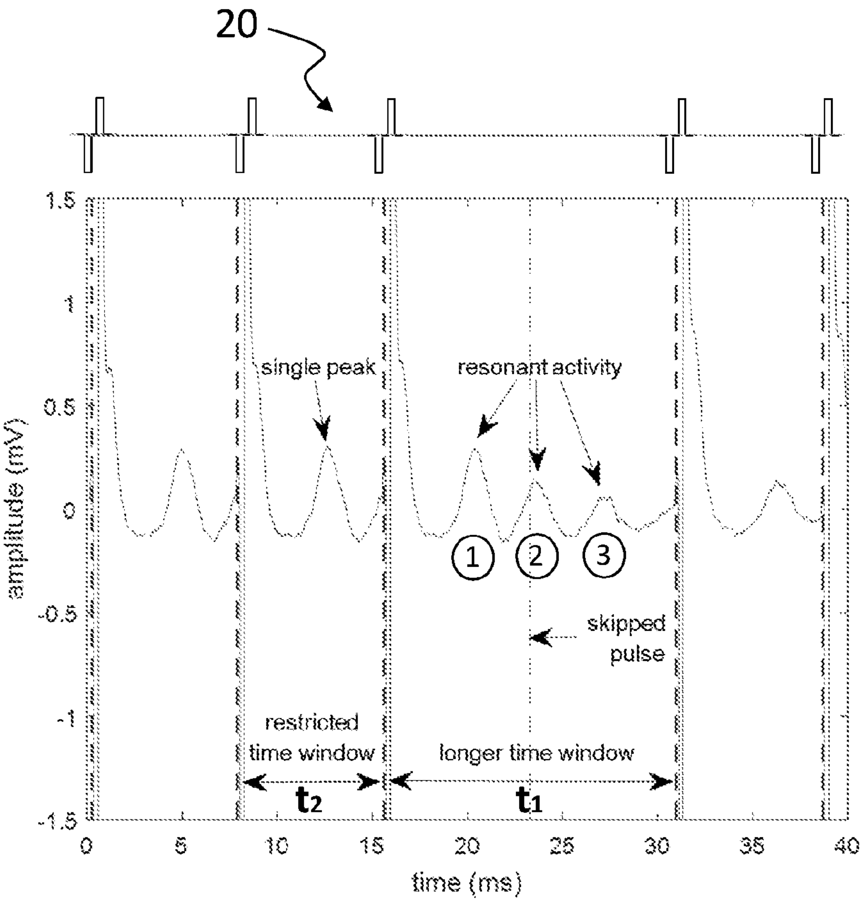
FIG. 2 is a graph illustrating resonance from a neural structure responsive to a patterned DBS signal.

FIG. 2 graphically illustrates an example therapeutic patterned DBS stimulus 20 and the associated evoked resonant response according to an embodiment of the present disclosure. The patterned stimulus 20 is shown above the graph to illustrate the correlation between stimulus and response. In the patterned stimulus, a single pulse has been omitted from an otherwise continuous 130 Hz pulse train. The pulse train therefore includes a plurality of bursts of pulses of continuous stimulation, each burst separated by a first time period t1, each of the plurality of pulses separated by a second time period t2. Continuation of the stimulus before and after omission of a pulse (or more than one pulse) maintains the therapeutic nature of the DBS, whilst the omission of a pulse allows for resonance of the ERNA to be monitored over several (3 in this example) resonant cycles before the next stimulation pulse interrupts this resonance. In other embodiments, two or more pulses of DBS may be omitted to see a longer duration of the ERNA response and therefore more cycles or resonance before the next stimulation pulse interrupts this resonance.

The inventors have found that this interruption or interaction of DBS pulses with ERNA has an interesting effect on ERNA which in turn may be linked to changes in therapeutic effects of DBS. It has been found the DBS pulses can be timed to occur at specific points in the waveform of ERNA to cause either a suppression, or a sustaining, or accentuation, or no effect at all. This indicates that by timing DBS pulses to occur at specific points in the ERNA waveform, the underlying neural circuits can be affected in different ways. Since a purpose of DBS is to modulate neural activity to produce a therapeutic effect, timing DBS pulses according to ERNA can provide a way to control the modulation and therefore to control therapy parameters.

Figure 3A:
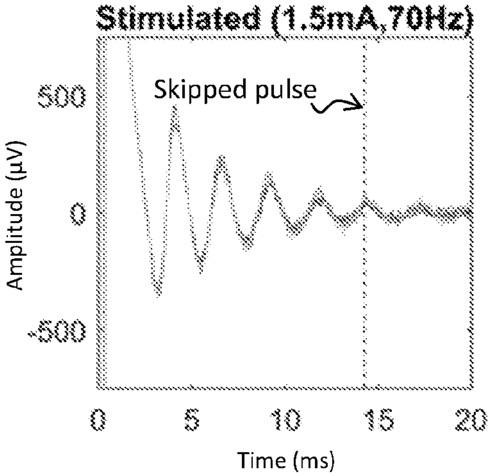
FIGS. 3A to 3G are graphs illustrating responses from a neural structure to patterned DBS signals.
Figure 3B:
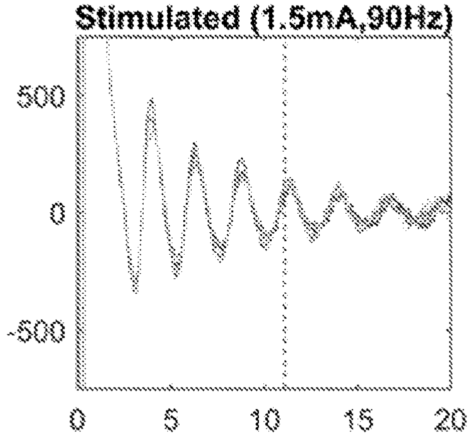
Figure 3C:
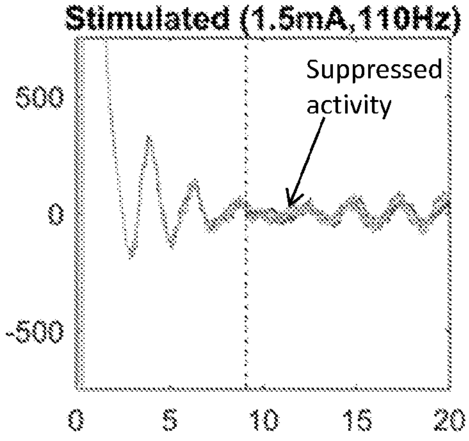
Figure 3D:
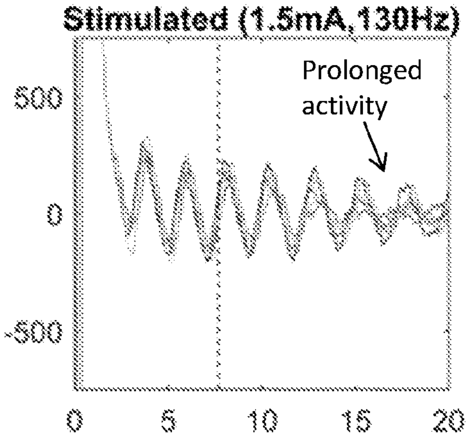

FIGS. 3A to 3G graphically illustrate the effect of interaction between DBS pulses and evoked resonant responses (ERNA). Specifically, these Figures illustrate how the timing of pulses relative to ERNA cause subsequent ERNA cycles to either be sustained, accentuated or suppressed. These results were obtained from a single patient by measuring ERNA in response to bursts of stimulation at different stimulation rates (20 pulses per burst at the rate indicated above each Figure, one burst per second for five seconds). In each of FIGS. 3A to 3C, five ERNA responses are superimposed over one another, each measured at the end of a 20 pulse burst. As with FIG. 2, the broken vertical line or skip line in each of FIGS. 3A to 3C represents the position at which the first skipped DBS pulse would have fallen if stimulation had continued at the same rate as that of the 20 preceding pulses. This broken line thereby provides an indication as to where DBS pulses of each burst were occurring in time relative to the waveform of the evoked neural activity (e.g. ERNA) during each DBS burst.

Figures 3E, 3F, 3G:
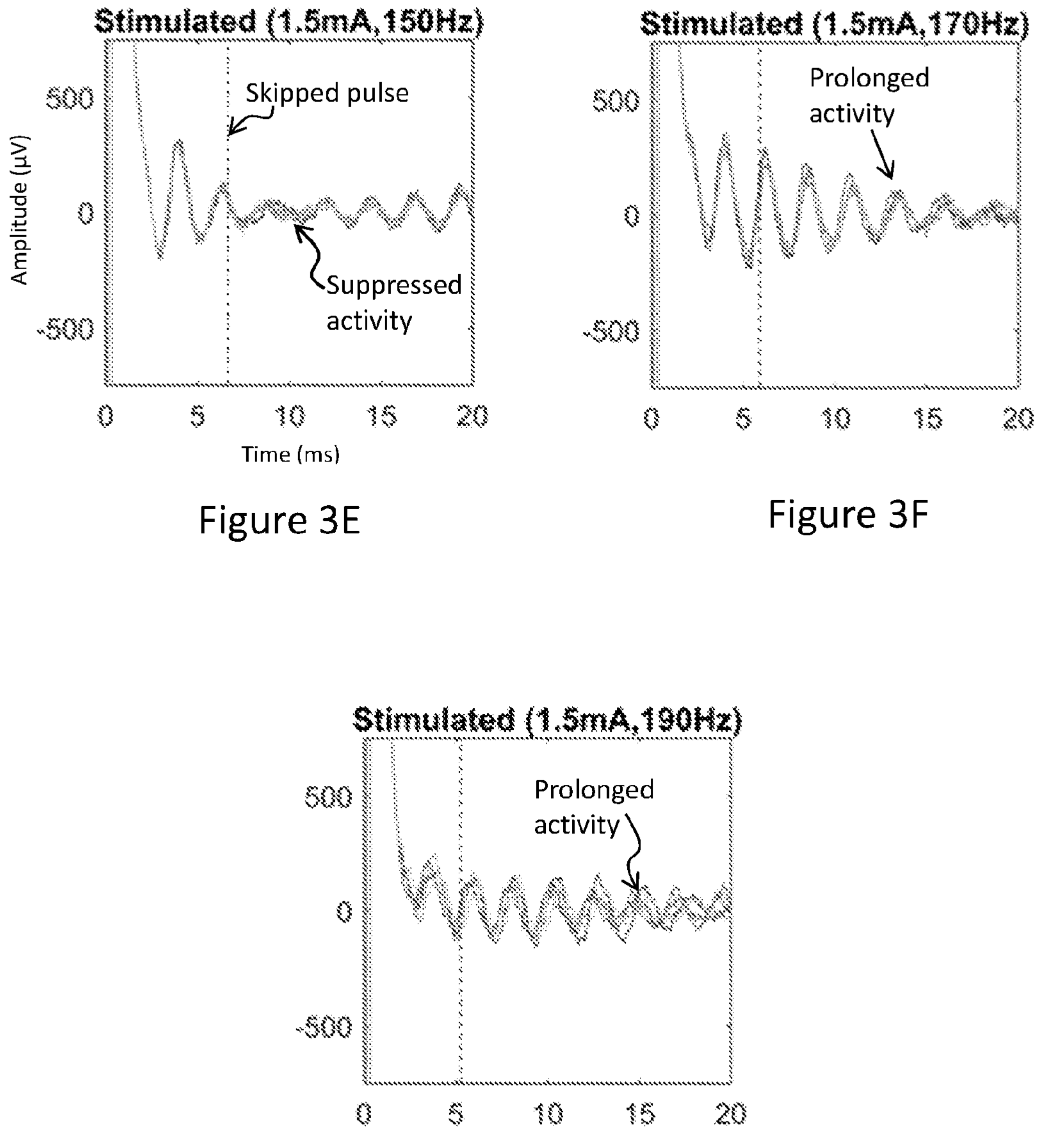

Referring to FIGS. 3C and 3E the evoked activity after cessation of the final pulse of the burst can be seen to be suppressed. This suppression coincides with the broken vertical line intersecting the neural waveform just after a peak, i.e. during a negative gradient of the observed ERNA. In contrast, in FIGS. 3D, 3F and 3G, the evoked neural activity after cessation of the final pulse of stimulation can be seen to be prolonged (sustained) or even amplified. This prolonging or amplification of neural activity coincides with the broken vertical line intersecting the waveform just before a peak, i.e. during a positive gradient of the observed ERNA waveform. This suggests that the timing (or phase) of a stimulus relative to the previously evoked response waveform can be tuned to affect the previously evoked response waveform in different ways (e.g. to suppress, sustain or amplify the previously evoked response).

The effects of interaction of stimulation pulses with ERNA appear to be dependent on how much ERNA evoked from a previous pulse has decayed before the onset of a subsequent pulse. For example, in the case of FIG. 3A, with a stimulation frequency of 70 Hz, the evoked waveform has substantially decayed at the vertical broken line. As such, it appears that the longer the delay between events evoking ERNA, the less interaction there is likely to be between a subsequent pulse of stimulation and the response (ERNA) evoked by a previous pulse.

Figure 4A:
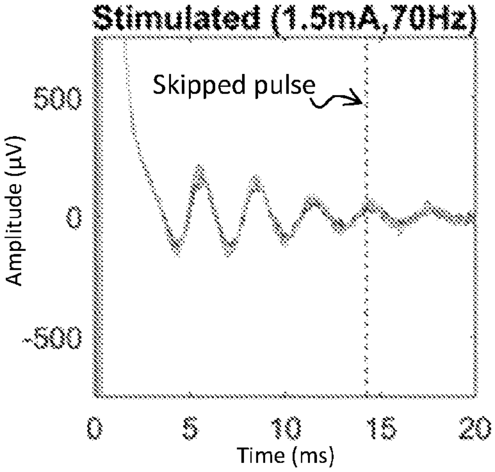
FIGS. 4A to 4G are graphs illustrating responses from a neural structure to patterned DBS signals.
Figure 4B:
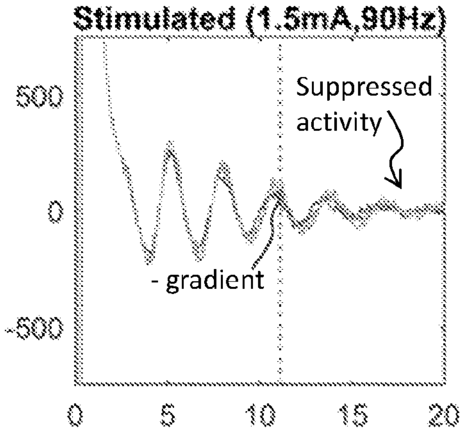
Figure 4C:
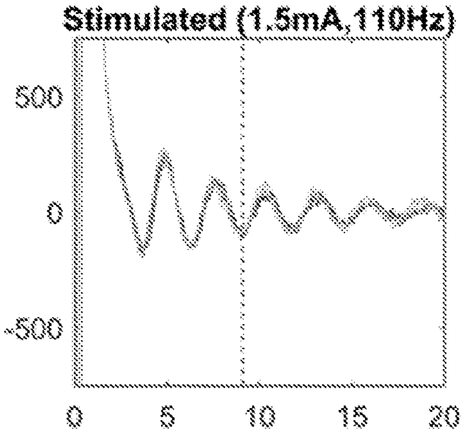
Figure 4D:
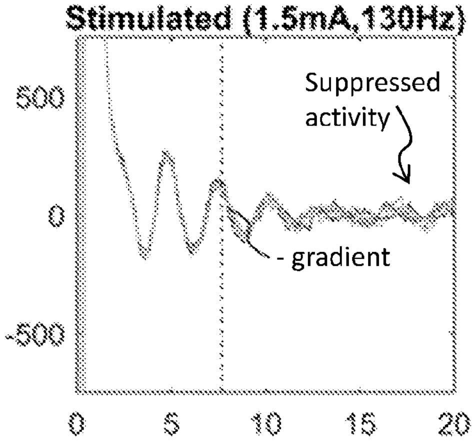
Figure 4E:
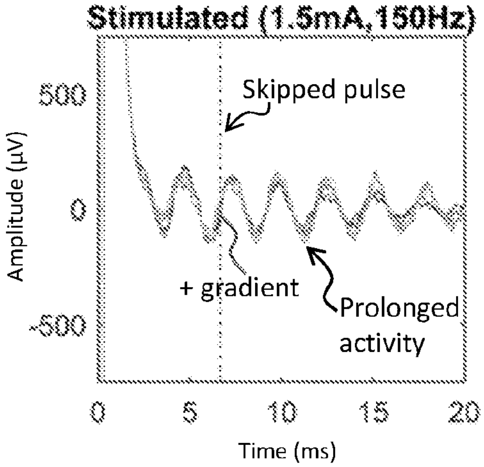
Figure 4F:
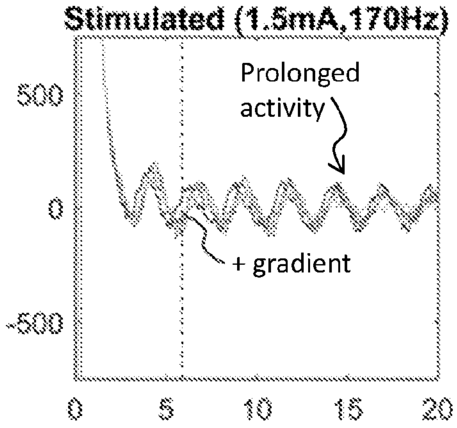
Figure 4G:
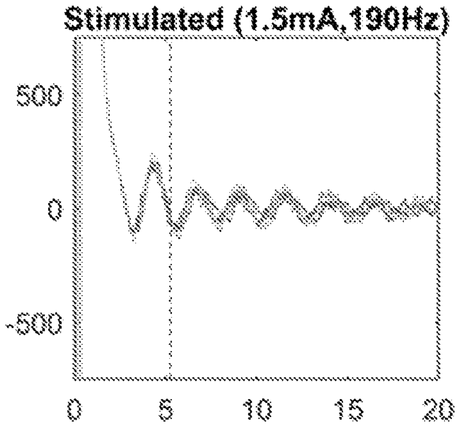
Figure 5:
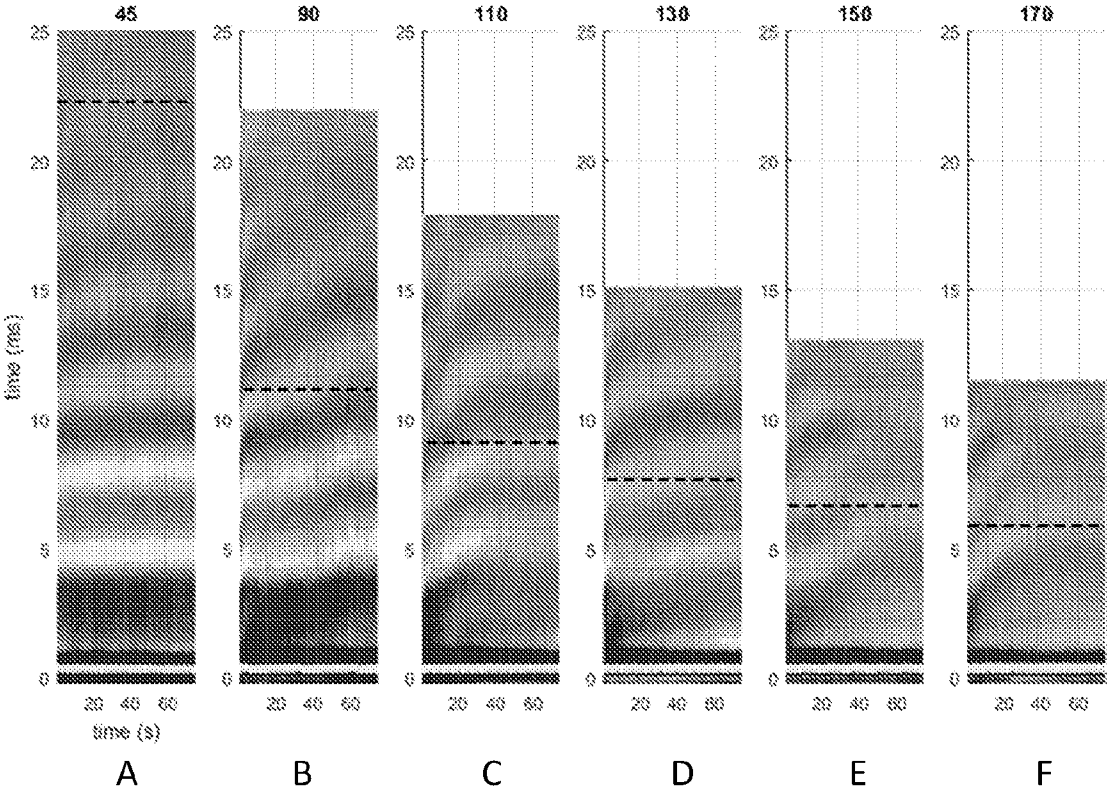
FIGS. 5A to 5F are time vs time plots of responses from a neural structure to patterned DBS signals.

FIGS. 4A to 4G graphically illustrate another example of the effect of interaction between DBS pulses and evoked resonant responses (ERNA) for a different Parkinson's disease patient under the same stimulation conditions as those described above with respect of FIGS. 3A to 3G. Referring to FIGS. 4B and 4D, the evoked activity (ERNA) after cessation of the final pulse of DBS is suppressed. This suppression again coincides with the broken vertical line intersecting the neural waveform just after a peak or during a negative gradient of the waveform. In contrast, like the patient of FIG. 3A to 3G, in FIGS. 4E and 4F, prolonging or sustaining of ERNA coincides with the broken vertical line intersecting the ERNA waveform just before a peak or during a positive gradient of the waveform.

Thus, FIGS. 4A to 4G provide further evidence of the interaction of DBS and ERNA. The inventors have determined that waveform characteristics of the ERNA (such as natural frequency, bandwidth, amplitude, rate of change of frequency and/or amplitude, etc.) are dependent on DBS.

FIGS. 5A to 5F provides another graphic example of the effect of interaction between DBS pulses and ERNA at stimulation frequencies of 45 Hz, 90 Hz, 110 Hz, 130 Hz, 150 Hz and 170 Hz respectively, as denoted at the top of each plot. A patient was stimulated by a pulse train comprising biphasic symmetric pulse waveforms delivered from a neurostimulator via an electrode lead, such as the 3387 electrode lead manufactured by Medtronic™, implanted in the subthalamic nucleus (STN) of the patient. Left and right hemispheres of the brain of the patient were stimulated alternately for a period of 75 seconds for each hemisphere at a series of discrete frequencies. FIGS. 5A to 5F show plots for the left hemisphere of the brain of the patient. The frequency of the stimulus was varied in a stepwise manner between 45 Hz and 170 Hz as denoted at the top of each plot. For the left hemisphere, a gap in stimulation of approximately 75 seconds was present between each frequency condition (during which the right hemisphere of the brain was stimulated). The DBS was patterned such that one pulse was skipped every second. By patterning DBS in this manner, ERNA can be measured over a longer time window, including around the time at which a pulse would normally occur but has been skipped. Such DBS patterning is described in detail in PCT (International) Patent Application Publication WO2018/027259.

ERNA is represented in these figures as time vs time plots. The vertical axis represents the time in milliseconds from the final pulse before each skipped pulse. The horizontal axis represents the time in seconds over which the pulse train was delivered at the specified frequency (75s total per frequency). The shading in each plot indicates ERNA amplitude, with lighter shading corresponding to positive amplitude and darker shading corresponding to negative amplitude. Six different stimulation rates were tested for 75s each and the dashed horizontal black line running across each spectrogram indicates when the skipped pulse would have coincided with the evoked neural response (ERNA) had the pulse not been skipped.

For all cases, ERNA peaks can be seen to move over time. Additionally, in FIGS. 5C, 5E and 5F at 110 Hz, 150 Hz and 170 Hz respectively, the movement in ERNA peaks appears to cease when the second peak reaches where the next DBS pulse would have occurred had it not been skipped. Additionally, in FIGS. 5E and 5F the ERNA peaks can be seen to be both suppressed and distorted, indicating that an interaction has occurred between the DBS pulse (occurring at 0 ms on the vertical axis) and the ERNA from the previous pulse.

These results indicate that the timing between the DBS pulses and the ERNA waveform can affect ERNA, and therefore the state of the underlying neural circuitry. It is believed that the accentuation (e.g. prolonging) and/or suppression of a neural response may underlie the therapeutic effects of DBS.

Having regard for the above, techniques have been developed for tailoring DBS such that pulses are timed to coincide with temporal features of ERNA. Specifically, embodiments of the present disclosure monitor ERNA responsive to an initial probe signal and generate subsequent therapeutic stimulation pulses to coincide with temporal features of future expected ERNA. Embodiments may continue to monitor ERNA during therapeutic stimulation, adjusting DBS in real time to maintain a temporal relationship between DBS and ERNA. The time point for applying each DBS pulse may be a specific phase or gradient of the ERNA waveform or some other temporal feature (e.g. a peak or trough in the ERNA waveform). Such time point may be specific to the patient and tailored based on the therapeutic effect of coinciding a DBS pulse at particular temporal points (e.g. peak, trough, zero crossing, positive/negative gradient) in the ERNA waveform.

In addition to adjusting DBS as described above, adjustments of other parameters of DBS, such as amplitude or phase width, may be made. Such adjustments may be made to reduce overall applied stimulation energy while maintaining a desired therapeutic effect. For example, timing the DBS pulse relative to a particular temporal feature of the ERNA waveform could provide an accentuated therapeutic effect, meaning that the overall energy required to be applied to the patient can be reduced, for example by reducing the amplitude of the applied DBS stimulus or the number of DBS pulses delivered over a given time interval.

Embodiments of the disclosure may implement an initial calibration phase in which it is determined at what point in time to apply the DBS pulses relative to ERNA. For example, a series of test stimuli with different temporal delays, patterns, or relationships may be applied to the patient.

Figure 6:
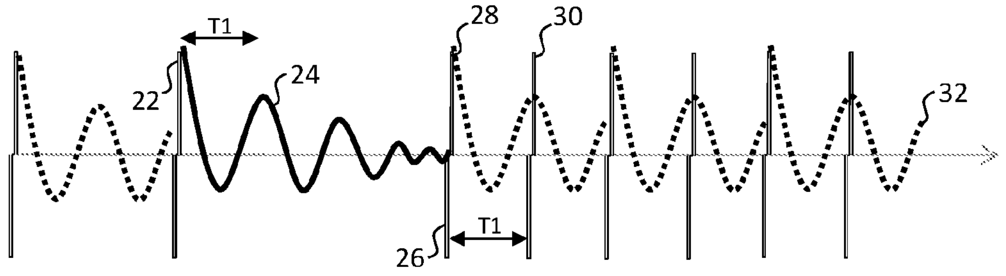
FIG. 6 illustrates a patterned stimulation signal according to an embodiment of the present disclosure.
Figure 7:
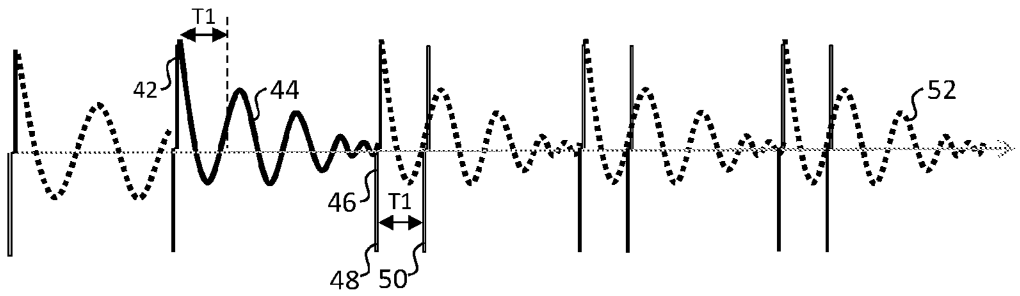
FIG. 7 illustrates a patterned stimulation signal according to an embodiment of the present disclosure.
Figure 8:
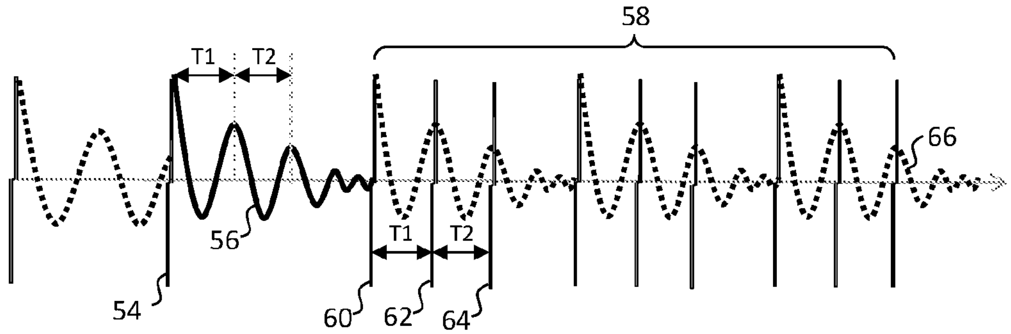
FIG. 8 illustrates a patterned stimulation signal according to an embodiment of the present disclosure.

FIGS. 6 to 8 provide a series of example stimulation profiles which may be implemented to take advantage of the above described phenomena.

FIG. 6 illustrates an example patterned probe stimulus for application to a target neural structure of the brain of a patient together with an example ERNA. The probe stimulus comprises a biphasic symmetric pulse waveform which may be delivered to a target neural structure in the brain of a patient. The probe stimulus is patterned so as to provide a period of no stimulation (stimulation gap) which is shown in FIG. 6 after pulse 22. During this time, in the absence of stimulation which might otherwise affect resonant activity, ERNA 24 can be analysed to identify one or more temporal features of the ERNA 24. In some embodiments, one or more temporal features at which to coincide pulses of DBS stimulation may be identified. In this example, the time T1 between the final pulse 22 before the stimulation gap and the first peak of the ERNA waveform 24 is identified as the temporal feature. In other embodiments, other temporal features can be identified, depending on the patient and/or other variables discussed above (e.g. a trough or a negative or positive gradient). A stimulation train 26 is then programmed and delivered which comprises two or more pulses 28, 30 per cycle, the second pulse 30 coinciding with the expected first peak of the expected ERNA waveform 32 evoked by the first pulse 28.

FIG. 7 shows another example patterned stimulus different to that of FIG. 6. In FIG. 7, a stimulation gap is provided after pulse 42, during which a response (ERNA) 44 can be analysed to identify one or more temporal features of the ERNA 44. In this example, the temporal feature of the ERNA 44 identified is a positive gradient of the first cycle of ERNA 44 denoted by the vertical broken line which intersects the ERNA 44. In other embodiments, other temporal features can be identified, depending on the patient and/or other variables discussed above. A time T1 between pulse 42 and a point on the positive gradient of the first cycle of ERNA 44 is thus identified. Based on this identified feature and the time T1, a stimulation train 46 is generated which comprises a plurality of pulses 48, 50 per cycle, the second pulse 40 coinciding with the expected positive gradient of the first cycle of expected ERNA 52 evoked by the first pulse 48 of the pair of pulses 48, 50. The pulses 48, 50 are grouped such that the second pulse 50 coincides with the expected position of the temporal feature of ERNA 52 evoked from the previous pulse 48, that feature being targeted by the programmed stimulation pattern. In this example, it can be seen that the generated therapeutic signal is aperiodic.

FIG. 8 shows another example patterned stimulus different to that of FIGS. 6 and 7. A stimulation gap is provided after pulse 54 of the patterned probe stimulus, during which ERNA 56 is analysed to identify one or more temporal features of the ERNA 56. In this example, peaks of the first and second cycles of ERNA 56 are chosen as first and second temporal features. As such, a time period T1 between the final pulse 54 and the peak of the first cycle of ERNA 56 is determined and the time period T2 between the peak of the first cycle of ERNA 56 and a peak of the second cycle of ERNA 56 is determined. It can be seen that the time periods T1 and T2 are slightly different in this example. As such, an aperiodic stimulation train 58 is generated which comprises three pulses 60, 62, 64, the second and third pulses coinciding with the expected peak of first and second cycles of the expected ERNA 66 evoked by the first pulse 60.

In each example, the stimulation trains 26, 46, 58 may be applied for a predetermined time. At which point, a further stimulation gap (i.e. period of no stimulation) may be provided, during which the analysis of resonant activity may be repeated to determine whether any changes should be made to therapy. During this stimulation gap, temporal features in the ERNA evoked by interaction of the final pulse of stimulation preceding the stimulation gap may be identified. Based on the timings of such temporal features, new stimulation trains may be generated and applied to the brain of the patient. Further, at any point, analysis of patient condition may be performed to determine the efficacy of the generated temporal stimulation patterns in the treatment of neural conditions.

It will be appreciated that FIGS. 6 to 8 provide just some of many examples of DBS stimulation profiles which may be generated in accordance with the present disclosure.

Figure 9:
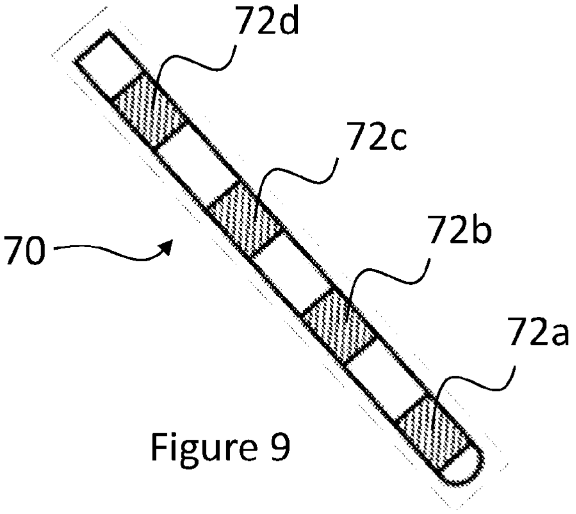
FIG. 9 is a schematic illustration of an electrode lead tip for implantation in a brain.

Having regard for the above, apparatus for implementing DBS stimulation profiles will now be described. A typical DBS electrode lead tip 70, such as that incorporated into the Medtronic™ DBS Lead Model 3387, is shown in FIG. 9. The lead tip 70 comprises a first electrode 72*a*, a second electrode 72*b*, a third electrode 72*c*, and a fourth electrode 72*d*. Once implanted into the brain, each of the electrodes 72*a*, 72*b*, 72*c*, 72*d* may be used to apply a stimulus to one or more neural structures or monitor and optionally record the evoked response (including ERNA) from neural circuits to the stimulus and the HFO activity measured from local field potentials in the brain. In other embodiments, leads with more electrodes or electrodes with different sizes or topologies may be used. In addition, one or more reference electrodes may be located at a remote site and used to complete the electrical circuit when one or more electrodes on the DBS lead are activated for stimulation or used for signal monitoring.

The target location for the lead tip 70 varies dependent on the neural structure. Example target structures include but are not limited to the subthalamic nucleus (STN), the substantia nigra pars *reticulata* (SNr), and the globus pallidus interna (GPi).

Figure 10:
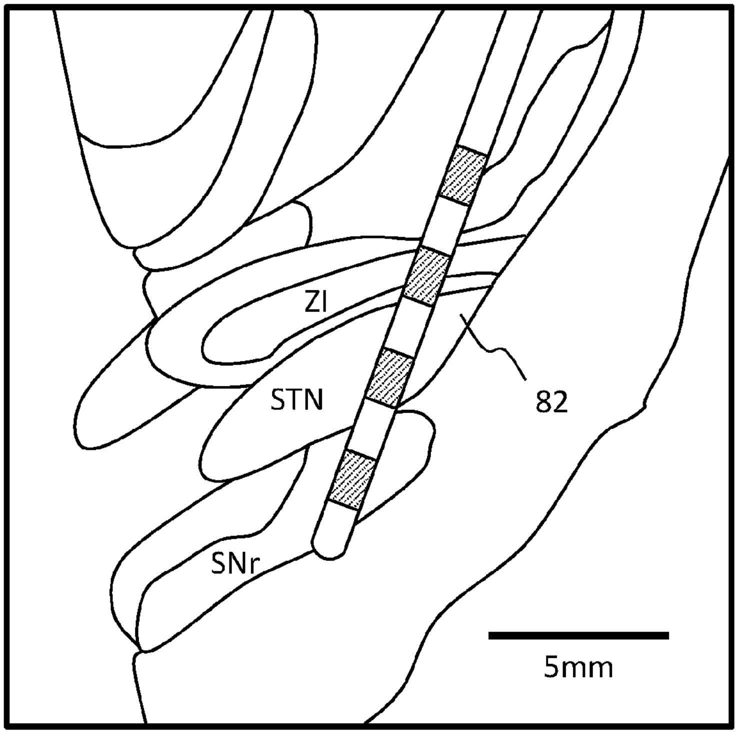
FIG. 10 is a schematic illustration of an electrode lead implanted in the subthalamic nucleus of a brain.

FIG. 10 shows the lead tip 70 implanted into a brain at a target structure, in this case the subthalamic nucleus (STN) 82. It will be appreciated that intersecting the electrode tip 70 with the subthalamic nucleus (STN) 82, which has a typical diameter of 5 to 6 mm, can be a very difficult surgical task. Techniques such as stereotactic imaging, microelectrode recordings, intraoperative x-ray imaging, and applying therapeutic stimulation whilst monitoring patient symptoms, are currently used to localise the electrode tip 70. However, these methods can lack accuracy. Additionally, existing methods usually require the patient to be awake for the procedure, since voluntary responses from the patient can be used to confirm that the electrode is at a suitable location relative to a target structure in the brain. For this reason, many potential recipients of DBS therapy turn down the option because they are not comfortable with having to be awake during the surgical procedure.

The accuracy of locating electrodes of the electrode tip 70 within a target structure can be greatly increased by using a series of patterned stimulations to generate and measure an evoked resonant response from a neural target. Such techniques can obviate the need for the patient to be awake during the implantation procedure, since an electrode can be located much more accurately at the correct location within the brain and relative to a target neural structure. This means that patients can be under sedation or general anaesthetic during the surgery since no patient feedback is required to locate the electrode to a satisfactory degree of accuracy.

Figure 11:
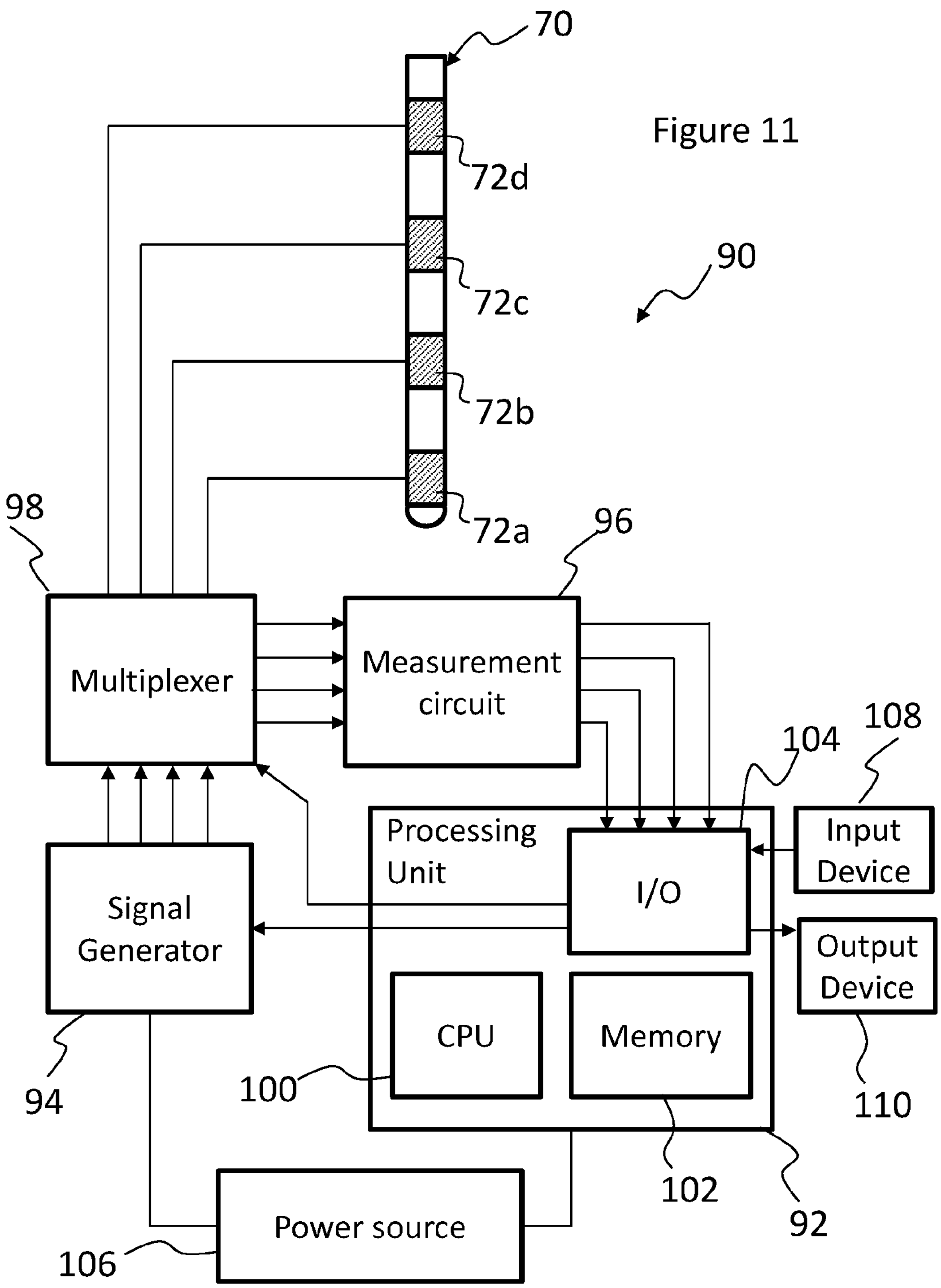
FIG. 11 is a schematic illustration of a system for administering DBS.

An example DBS delivery system 90 according to an embodiment of the present disclosure is illustrated in FIG. 11. The system 90 comprises the lead tip 70 of FIG. 9 including the plurality of integrated electrodes 72*a*, 72*b*, 72*c*, 72*d*, together with a processing unit 92, a signal generator 94, a measurement circuit 96 and an optional multiplexer 98. The processing unit comprises a central processing unit (CPU) 100, memory 102, and an input/output (I/O) bus 104 communicatively coupled with one or more of the CPU 100 and memory 102.

In some embodiments, the multiplexer 98 is provided to control whether the electrodes 72*a*, 72*b*, 72*c*, 72*d* are connected to the signal generator 94 and/or to the measurement circuit 96. In other embodiments the multiplexer may not be required. For example, the electrodes 72*a*, 72*b*, 72*c*, 72*d* may instead be connected directly to both the signal generator 94 and the measurement circuit 96. Although in FIG. 13 all of the electrodes 72*a*, 72*b*, 72*c*, 72*d* are connected to the multiplexer 98, in other embodiments, only one or some of the electrodes 72*a*, 72*b*, 72*c*, 72*d* may be connected.

The measurement circuit 96 may include one or more amplifiers and digital signal processing circuitry including but not limited to sampaling circuits for measuring neural responses to stimulation, including ERNA. The measurement circuit 96 may be configured to measure ERNA in the frequency range of between 100 and 1000 Hz, for example 200 to 500 Hz, or 250 to 450 Hz, or 250 to 400 Hz.

In some embodiments the measurement circuit 96 may also be configured to extract other information from received signals, including local field potentials for measurement of HFOs and the like. The measurement circuit 96 may also be used in conjunction with the signal generator 94 to measure electrode impedances. The measurement circuit 96 may be external to or integrated within the processing unit 92. Communication between the measurement circuit 96 and/or the signal generator 94 on the one hand and the I/O port on the other may be wired or may be via a wireless link, such as over inductive coupling, Wi-Fi™, Bluetooth™ or the like. Power may be supplied to the system 90 via at least one power source 106. The power source 106 may comprise a battery such that elements of the system 90 can maintain power when implanted into a patient.

The signal generator 94 is coupled via the multiplexer 98 to one or more of the electrodes 72*a*, 72*b*, 72*c*, 72*d* and is operable to deliver electrical stimuli to respective electrodes based on signals received from the processing unit 92. To this end, the signal generator 94, the multiplexer 98 and the processing unit 92 are also communicatively coupled such that information can be transferred therebetween.

Whilst the signal generator 94, multiplexer 98, and the processing unit 92 in FIG. 11 are shown as separate units, in other embodiments the signal generator 94 and multiplexer may be integrated into the processing unit 92. Furthermore, either unit may be implanted or located outside the patient's body.

The system 90 may further comprise one or more input devices 108 and one or more output devices 110. Input devices 108 may include but are not limited to one or more of a keyboard, mouse, touchpad and touchscreen. Examples of output devices include displays, touchscreens, light indicators (LEDs), sound generators and haptic generators. Input and/or output devices 108, 110 may be configured to provide feedback (e.g. visual, auditory or haptic feedback) to a user related, for example, to characteristics of ERNA or subsequently derived indicators (such as proximity of the electrode 70 relative to neural structures in the brain. To this end, one or more of the input devices 108 may also be an output device 110, e.g. a touchscreen or haptic joystick. Input and output devices 108, 110 may also be wired or wirelessly connected to the processing unit 92. Input and output devices 108, 110 may be configured to provide the patient with control of the device (i.e. a patient controller) or to allow clinicians to program stimulation settings, and receive feedback of the effects of stimulation parameters on ERNA and/or HFO characteristics.

One or more elements of the system 90 may be portable. One or more elements may be implantable into the patient. In some embodiments, for example, the signal generator 94 and lead 70 may be implantable into the patient and the processing unit 92 may be external to the patient's skin and may be configured for wireless communication with the signal generator via RF transmission (e.g. induction, Bluetooth™, etc.). In other embodiments, the processing unit 92, signal generator 94 and lead 70 may all be implanted within the patient's body. In any case, the signal generator 94 and/or the processing unit 92 may be configured to wirelessly communicate with a controller (not shown) located external to the patient's body.

Having regard for the above, embodiments of the present disclosure provide a method and system for applying bespoke neurostimulation to a target neural structure of a brain of a patient using the lead tip 70 based on an analysis of an electrical response measured at the lead tip 70 to a probe signal applied at or near the target neural structure.

Figure 12:
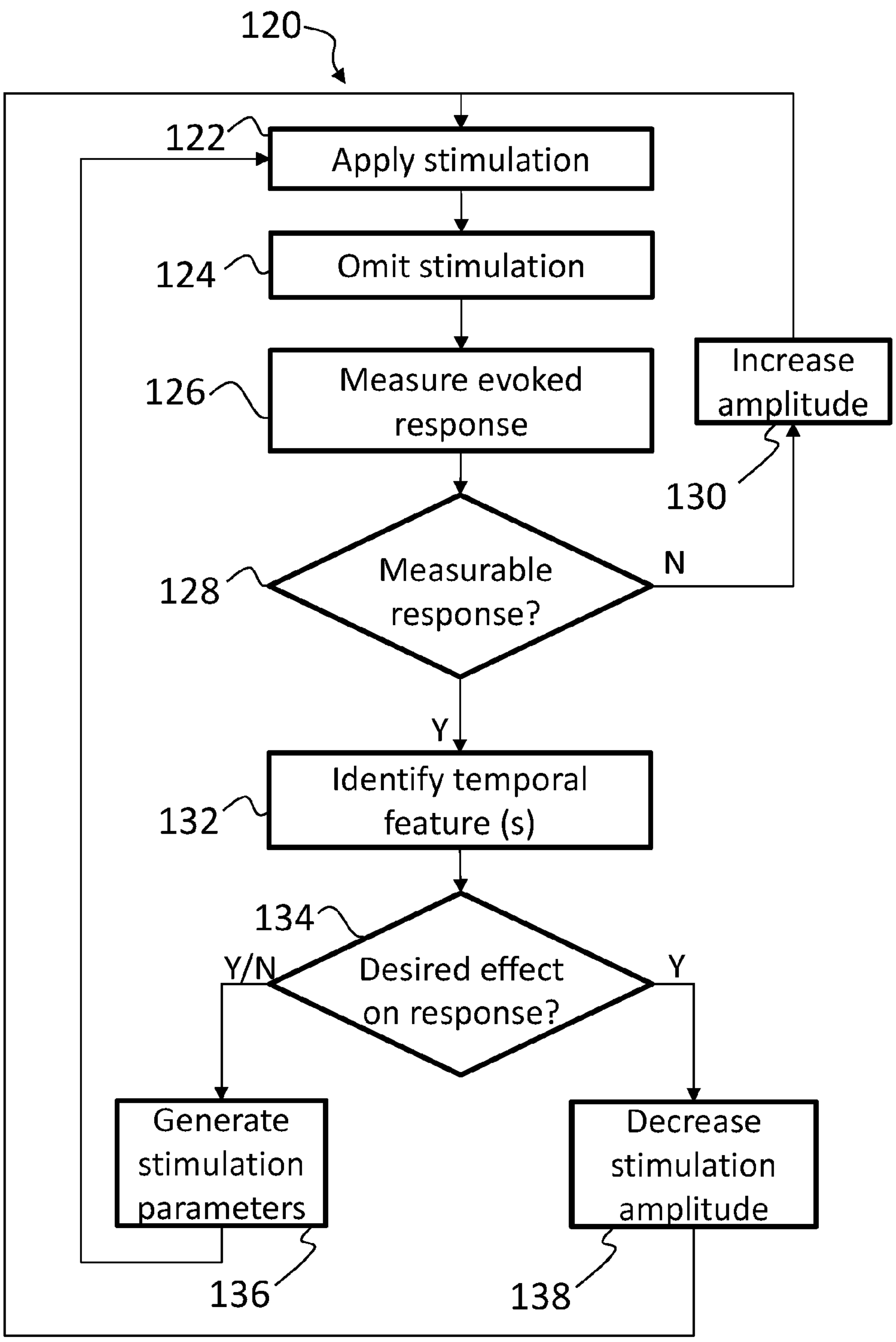
FIG. 12 is a flow diagram illustrating a process for setting a stimulation profile at a lead tip implanted in the brain.

FIG. 12 shows an example of a process 120 for applying programmed neurostimulation. The process begins at step 122 where a probe signal is applied to an electrode of the lead tip 70. The probe signal may comprise therapeutic stimulation or may be applied specifically for analysis of electrical activity evoked by a neural structure in the brain.

After applying the probe signal, at step 124 stimulation may be ceased for a period, for example by skipping or omitting one or more pulses of stimulation. Doing so may enable ERNA to be measured during the period of no stimulation. Subsequent to ceasing stimulation, at step 126, evoked responses, including ERNA, are measured at one or more electrodes of the lead tip 70. For example, evoked responses in the frequency range of 100 to 1000 Hz, for example 200 to 500 Hz, or 250 to 450 Hz, or 250 to 400 Hz, may be monitored and measured.

The process of applying stimulation 122, omitting pulses of stimulation 124 and measuring an evoked response 126 may be repeated a predetermined number of times, such as 10 times. During this time, the effect of stimulation on ERNA may be characterised. The evoked response may be measured at the same electrode as that used to apply the stimulus or may be measured at one or more different electrodes. If at step 128, there is no measureable response to the stimulation applied at step 122, then at step 130 the amplitude of the stimulation applied at step 122 may be increased and steps 122, 124 and 126 repeated.

Once it is determined that a response is present at one or more of the electrodes of the lead tip 70, at step 132, one or more temporal features of the measured response may be identified as being affected by the stimulation applied at step 122. Such temporal features may, for example, comprise a peak a trough, a crossing of the response through a predetermined amplitude, or a gradient of the response. An effect may comprise a suppression, a sustaining (or prolonging) or an accentuation (or amplification) of an evoked response at the temporal feature, which may be caused by an interaction between applied stimulation and the evoked response.

At step 134, a determination may be made as to whether the effect at the identified temporal feature(s) is desired. For example, a determination as to whether a suppression, sustaining or accentuation leads to an improvement of the neural condition of the patient in question. For example, suppression, sustaining or accentuation may be associated with an improvement in the patient's motor symptoms, such as rigidity, bradykinesia, or tremor as determined through clinical observations. The link between each of these effects may be patient specific.

Based on the determination at step 134, at step 136 a therapeutic stimulus may be generated comprising a plurality of pulses for application at step 122. The therapeutic stimulus may be programmed such that pulses of the stimulus coincide with temporal features expected to be present in a response evoked by the stimulus being generated. For example, the time period between two or more of pulses in the stimulus may be chosen based on the duration between the completion of the probe signal and the temporal feature identified at step 132. As described with reference to FIGS. 6 to 8, stimulation regimes may vary considerably depending on the patient, the measured evoked response, the effect of interaction between applied stimulation and any evoked response etc. In some embodiments, stimulation parameters may be generated only if it is determined that the applied stimulation at step 122 is not having the desired effect on the measured response. In some embodiments, stimulation parameters may be generated regardless of whether the desired effect is determined at step 134.

If it is found at step 134 that the applied stimulation is having a desired effect on stimulation, then at step 138, one or more other stimulation parameters, such as stimulation amplitude in applied stimulation at step 122, may be adjusted. For example, stimulation amplitude may be decreased so as to reduce the total charge or energy provided by the stimulus to the patient. In some embodiments, this may be done to reduce the energy applied to below a therapeutic threshold whilst still obtaining measurements of evoked response which may provide information concerning the patient's natural state (without therapy). In some embodiments, stimulation amplitude may be decreased to a point at which therapy is still being administered but the side effects associated with such therapy are reduced because the total energy being applied to the patient is reduced.

At step 122 the adjusted or newly generated stimulation may be applied to the patient via the lead tip 70 for a predetermined period of time before the process 120 is repeated. The process 120 may be repeated continuously, i.e. applying the predetermined or "programmed" stimulation for a period of time and continuously performed updates and adjustments based on analysis performed during patterned (omitted) periods of the stimulus. In such cases, parameters of stimulation may be continuously updated to optimise patient condition to a preferred state. Alternatively, the process 120 may be repeated once in a calibration phase during set up of the system 90. It will be appreciated that FIG. 12 provides just one non limiting example of a process which may be implemented to generate and apply tailored therapeutic neurostimulation to a patient.

In any case, it will be appreciated that method and systems described herein enable the generation of bespoke stimulation profiles based on measured evoked responses of a patient.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of neurostimulation, comprising:

a. applying a probe signal to an electrode implanted in or near a target neural structure of the brain;

b. detecting a first response from the target neural structure evoked by the probe signal;

c. determining a first time period between application of the probe signal and a first temporal feature of the first response;

d. generating a therapeutic signal comprising a plurality of pulses, at least two of the plurality of pulses separated by the first time period;

e. applying the therapeutic signal to the electrode or another electrode implanted in or near the target neural structure.

2. The method of claim 1, further comprising:

repeating steps a to d.

3. The method of claim 2, further comprising continuously applying the therapeutic signal to the electrode between repetitions of steps a to d.

4. The method of claim 1, wherein at least three of the plurality of pulses are separated by the first time period.

5. The method of claim 1, further comprising:

f. determining a second time period between application of the probe signal and second temporal feature of the first oscillatory response, wherein at least two of the plurality of pulses are separated by the second time period.

6. The method of claim 5, wherein a first one of the at least two of the plurality of pulses separated by the first time period and a first one of the at least two of the plurality of pulses separated by the second time period are the same pulse.

7. The method of claim 1, wherein the probe signal has a fixed amplitude.

8. The method of claim 1, wherein completion of application of the probe signal and commencement of application of the therapeutic signal are separated by a measurement time period in which no signal is applied to the electrode or the other electrode implanted in or near the target neural structure.

9. The method of claim 1, further comprising:
detecting a second response from the target neural structure evoked by the therapeutic signal; and
determining a difference between a common temporal feature in the first and second responses.

10. The method of claim 9, wherein the difference comprises a difference in amplitude of the first and second responses.

11. The method of claim 10, wherein determining the difference comprises determining that the common temporal feature is suppressed in the second response relative to the first response.

12. The method of claim 9, further comprising:
adjusting the amplitude of the therapeutic signal in dependence on the difference.

13. The method of claim 1, further comprising, after detecting the first response and before determining the first time period:
determining that the amplitude of the first response is below a threshold amplitude; and
increasing the amplitude of and re-applying the probe signal until the amplitude of the first response is at or greater than the threshold amplitude.

14. The method of claim 1, wherein a frequency of pulses of the plurality of pulses other than the at least two pulses separated by the first time period is set such that an average frequency of pulses in the plurality of pulses is within a threshold range of a predetermined therapeutic frequency.

15. The method of claim 14, wherein the predetermined therapeutic frequency is between 70 Hz and 200 Hz.

16. The method of claim 1, wherein the temporal feature is one of:
a peak in the response;
a trough in the response;
a crossing of the response through a predetermined amplitude;
a gradient of the response.

17. A method of neurostimulation, comprising:
applying a stimulus to an electrode implanted in or near a target neural structure of the brain, the stimulus comprising a plurality of pulses;
detecting a response from the target neural structure evoked by the stimulus;
determining a first time period between application of the stimulus and a first temporal feature of the first response;
adjusting the stimulus such that at least two of the plurality of pulses are separated by the first time period;
applying the adjusted stimulus to the electrode.

18. A neurostimulation system, comprising:
a lead having at least one electrode adapted for implantation in or near a target neural structure in the brain;
a signal generator selectively coupled to one or more of the at least one electrode and configured to:
a. apply a probe signal to one of the at least one electrode implanted in or near the target neural structure of the brain; and
one or more processors configured to:
b. detect at the at least one electrode a first response from the target neural structure, the first response evoked by the probe signal;
c. determine a first time period between application of the probe signal and a first temporal feature of the first response; and
d. generate a therapeutic signal comprising a plurality of pulses, at least two of the plurality of pulses separated by the first time period,
the signal generator further configured to:
e. apply the therapeutic signal to the at least one electrode or another electrode implanted in or near the target neural structure.

19. The system of claim 18, the signal generator and the one or more processors further configured to:
repeat steps a to d.

20. The system of claim 19, wherein the signal generator is configured to continuously apply the therapeutic signal to the electrode between repetitions of steps a to d.

21. The system of claim 18, wherein at least three of the plurality of pulses are separated by the first time period.

22. The system of claim 18, wherein the one or more processors is further configured to:
f. determine a second time period between application of the probe signal and second temporal feature of the first response, wherein at least two of the plurality of pulses are separated by the second time period.

23. The system of claim 22, wherein a first one of the at least two of the plurality of pulses separated by the first time period and a first one of the at least two of the plurality of pulses separated by the second time period are the same pulse.

24. The system of claim 18, wherein the probe signal has a fixed amplitude.

25. The system of claim 18, wherein completion of application of the probe signal and commencement of application of the therapeutic signal are separated by a measurement time period in which no signal is applied to the electrode or the other electrode implanted in or near the target neural structure.

26. The system of claim 18, wherein the one or more processors are further configured to:
detect a second response from the target neural structure, the second response evoked by the therapeutic signal; and
determine a difference between a common temporal feature in the first and second responses.

27. The system of claim 26, wherein the difference comprises a difference in amplitude of the first and second responses.

28. The system of claim 26, wherein determining the difference comprises determining that the common temporal feature is suppressed in the second response relative to the first response.

29. The system of claim 26, the one or more processors further configured to:
adjust the amplitude of the therapeutic signal in dependence on the difference.

30. The system of claim 18, the one or more processors further configured to, after detecting the first response and before determining the first time period:
determine that the amplitude of the first response is below a threshold amplitude; and
increase the amplitude of the probe signal being applied by the signal generator until the amplitude of the first response is at or greater than the threshold amplitude.

31. The system of claim 18, wherein a frequency of pulses of the plurality of pulses other than the at least two pulses separated by the first time period is set such that an average frequency of pulses in the plurality of pulses is within a threshold range of a predetermined therapeutic frequency.

32. The system of claim 31, wherein the predetermined therapeutic frequency is between 70 Hz and 200 Hz.

33. The system of claim 18, wherein the temporal feature is one of:

a peak in the response;

a trough in the response;

a crossing of the response through a predetermined amplitude;

a gradient of the response.

* * * * *